United States Patent [19]

Browne

[11] Patent Number: 4,470,986

[45] Date of Patent: Sep. 11, 1984

[54] CERTAIN IMIDAZO (1,5-a) PYRIDINE ALIPHATIC CARBOXYLIC ACID DERIVATIVES AND THEIR USE AS SELECTIVE THROMBOXANE INHIBITORS

[75] Inventor: Leslie J. Browne, Morris Plains, N.J.

[73] Assignee: Ciba-Geigy Corporation, Ardsley, N.Y.

[21] Appl. No.: 451,903

[22] Filed: Dec. 21, 1982

[51] Int. Cl.$^3$ ..................... A61K 31/44; C07D 471/04
[52] U.S. Cl. .................................... 424/256; 546/121
[58] Field of Search ........................ 546/121; 542/435; 424/256

[56] References Cited

U.S. PATENT DOCUMENTS

| 3,790,586 | 2/1974 | Irikura et al. | |
| 4,226,878 | 10/1980 | Iizuka et al. | 424/273 R |
| 4,256,757 | 3/1981 | Hayashi et al. | 424/273 R |
| 4,444,775 | 4/1984 | Ford | 424/256 |

FOREIGN PATENT DOCUMENTS

| 15171 | 9/1980 | European Pat. Off. . |
| 68386 | 1/1983 | European Pat. Off. . |
| 2016452 | 9/1979 | United Kingdom . |
| 2038821 | 7/1980 | United Kingdom . |

OTHER PUBLICATIONS

P. Blatcher, et al., Tetrahedron Letters 21, 2195 (1980).
G. J. Durant, et al., J. Medicinal Chemistry 16, 1272 (1973).
W. W. Paudler, et al., J. Heterocyclic Chemistry 3, 33 (1966).
O. Fuentes, et al., J. Org. Chemistry 40, 1210 (1975).

*Primary Examiner*—John M. Ford
*Assistant Examiner*—Bernard Dentz
*Attorney, Agent, or Firm*—Norbert Gruenfeld

[57] ABSTRACT

Disclosed are e.g. 5-(tetrazolylalkyl, hydroxycarbamoylalkyl)imidazo[1,5-a]-pyridines, and methods of synthesis. Said compounds are useful as selective thromboxane synthetase inhibitors for the treatment of diseases such as cerebral ischaemia, shock, thrombosis and ischaemic heart disease.

17 Claims, No Drawings

CERTAIN IMIDAZO (1,5-a) PYRIDINE ALIPHATIC CARBOXYLIC ACID DERIVATIVES AND THEIR USE AS SELECTIVE THROMBOXANE INHIBITORS

SUMMARY OF THE INVENTION

The present invention is concerned with imidazo[1,5-a]pyridine derivatives representing potent and highly specific thromboxane synthetase inhibitors.

The foregoing advantages and attributes render the imidazo [1,5-a]pyridine derivatives of this invention particularly useful when administered, alone or in combination, to mammals, e.g. for the treatment or prevention of diseases responsive to the inhibition of thromboxane synthetase comprising cardiovascular disorders such as thrombosis, atherosclerosis, cerebral ischaemic attacks, myocardial infarction, angina pectoris, hypertension; respiratory disorders, such as asthma; inflammatory disorders; carcinoma, such as tumor metastasis; and migraine headache.

This invention thus relates to imidazo[1,5-a]pyridine derivatives useful as selective thromboxane synthetase inhibitors, processes for preparing same, pharmaceutical compositions comprising said compounds, and methods of treating diseases responsive to inhibition of thromboxane synthetase by administration of said compounds and compositions to mammals.

Particularly the invention relates to imidazo[1,5-a]pyridine derivatives of formula I

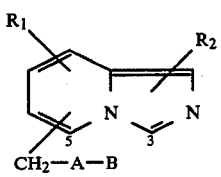

(I)

or 5,6,7,8-tetrahydro derivatives thereof, wherein $R_1$ is hydrogen, halogen, lower alkyl, lower alkoxy, hydroxy or aryl-lower alkoxy; $R_2$ is hydrogen, halogen, or lower alkyl; A is straight chain or branched alkylene of 1 to 12 carbon atoms, alkynylene or alkenylene of 2 to 12 carbon atoms each; B represents 5-tetrazolyl, hydroxycarbamoyl, 4,5-dihydro-2-oxazolyl or 4,5-dihydro-2-oxazolyl substituted by lower alkyl; or salts, especially pharmaceutically acceptable salts thereof.

DESCRIPTION OF THE PREFERRED EMBODIMENTS

Preferred embodiments of this invention relate to compounds of formula I wherein the group $CH_2$-A-B is attached at the 5 position. Very useful as thromboxane synthetase inhibitors are compounds of formula I wherein A is straight or branched alkylene of 1 to 12 carbon atoms.

Particularly, preferred are compounds of formula II

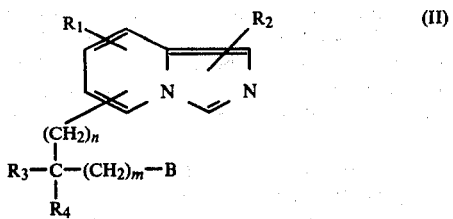

(II)

or 5,6,7,8-tetrahydro derivatives thereof, wherein $R_1$, $R_2$, $R_3$ and $R_4$ are hydrogen or lower alkyl of 1 to 4 carbon atoms; n is 1 to 7; m is 0 or 1; B represents 5-tetrazolyl, hydroxycarbamoyl, 4,5-dihydro-2-oxazolyl or 4,5-dihydro-2-oxazolyl substituted by lower alkyl; or pharmaceutically acceptable salts thereof.

Especially preferred are compounds of formula II or 5,6,7,8-tetrahydro derivatives thereof, wherein $R_1$, $R_2$, $R_3$, $R_4$ are hydrogen, methyl or ethyl; $(CH_2)_n$ is propylene, butylene, pentylene or hexylene; m is 0 or 1; B represents 5-tetrazolyl, hydroxycarbamoyl, or 4,5-dihydro-2-oxazolyl; or pharmaceutically acceptable salts thereof.

Preferred in turn, are the compounds of formula II wherein the group

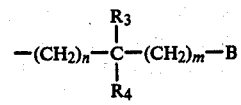

is attached at the 5-position.

Exceedingly useful are compounds of formula III, or 5,6,7,8-tetrahydro derivatives thereof,

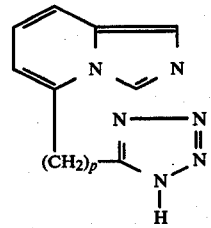

(III)

wherein p is 3 to 8; or pharmaceutically acceptable salts thereof.

Especially valuable are compounds of formula III, or 5,6,7,8-tetrahydro derivatives thereof, wherein p is 4,5 or 6; or pharmaceutically acceptable acid addition salts thereof.

The general definitions used herein have the following meanings within the scope of the present invention.

A "straight chain or branched alkylene" represents $C_{1-12}$ alkylene preferably propylene, butylene, pentylene or hexylene, said radicals being unsubstituted or substituted by one or more lower alkyl groups with the proviso that the total number of carbon atoms equals no more than 12.

The term "straight chain or branched alkenylene" represents $C_{2-12}$ alkenylene preferably propenylene, 1- or 2-butenylene, 1- or 2-pentenylene, 1-, 2- or 3-hexenylene, said radicals being unsubstituted or substituted by one or more lower alkyl groups with the proviso that the total number of carbon atoms equals no more than 12.

The term "straight chain or branched alkynylene" represents $C_2$-$C_{12}$ alkynylene preferably propynylene, 1- or 2-butynylene, 1- or 2-pentynylene, 1-, 2- or 3-hexynylene, said radicals being unsubstituted or substituted by one or more lower alkyl groups with the proviso that the total number of carbon atoms equal no more than 12.

The term "lower" referred to above and hereinafter in connection with organic radicals or compounds respectively defines such with up to and including 7, preferably up to and including 4 and advantageously one or two carbon atoms.

A lower alkyl group preferably contains 1-4 carbon atoms and represents for example ethyl, propyl, butyl or advantageously methyl.

An aryl group such as in aryl-lower alkoxy represents preferably phenyl or phenyl mono- or di-substituted by lower alkyl, halogen or lower alkoxy.

An aryl lower alkoxy group advantageously represents benzyloxy.

A lower alkoxy group preferably contains 1-4 carbon atoms and represents for example methoxy, propoxy, isopropoxy or advantageously ethoxy.

Halogen is preferably fluoro and chloro, but may also represent bromo or iodo.

Pharmaceutically acceptable salts are preferably metal or ammonium salts of said compounds of formula I when B represents 5-tetrazolyl or hydroxycarbamoyl, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium bases, e.g., methylamine, diethylamine, triethylamine, dicyclohexylamine, triethanolamine, ethylenediamine, tris-(hydroxymethyl)-aminomethane or benzyl-trimethylammonium hydroxide. The compounds of Formula I form acid addition salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively inhibiting the release of thromboxane through selective inhibition of thromboxane synthetase in mammals. The compounds are thus useful for treating diseases responsive to thromboxane synthetase inhibition in mammals including man.

These effects are demonstrable in vitro assay tests or in vivo animal tests during advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 and 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}$C-Arachidonic acid is incubated with an enzyme preparation consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin $E_2$ ($PGE_2$) is reduced to a mixture of Prostaglandin $F_2\alpha$ and $F_2\beta$ [$PGF_2(\alpha+\beta)$] by addition of sodium borohydride. The radioactive products and excess substrate are extracted into ethyl acetate; the extract is evaporated to dryness; the residue is dissolved in acetone, spotted on thin-layer plates and chromatographed in the solvent system toluene: acetone: glacial acetic acid (100 volumes: 100 volumes: 3 volumes). The radioactive zones are located; those corresponding to Thromboxane $B_2$ ($TxB_2$) and $PGF_2$ $\alpha+\beta$ are transferred to liquid scintillation vials and counted. The ratio of counts for $TxB_2/PGF_2$ $\alpha+\beta$ is calculated for each concentration of test compound and $IC_{50}$ values are determined graphically as the concentration of test compound at which the ratio of $TxB_2/PGF_2$ $\alpha+\beta$ is reduced to 50% of the control value.

The in-vitro effect on prostaglandin cyclooxygenase is measured by a modification of the method of Takeguchi et al described in Biochemistry 10, 2372 (1971); the testing procedure is as follows:

Lyophilized sheep seminal vesicle microsomes are utilized as the prostaglandin-synthesizing enzyme preparation. The conversion of $^{14}$C-arachidonic acid to $PGE_2$ is measured. Test compounds (dissolved in buffer, or if necessary, in small amount of ethanol) are added to the incubation mixture. The prostaglandins are extracted and separated by thin-layer chromatography; the plates are scanned, the radioactive zones corresponding to $PGE_2$ are transferred to liquid scintillation vials and counted for radioactivity. $IC_{50}$ values for inhibition are determined graphically as the concentration of test compound causing a 50% reduction in the amount of $PGE_2$ synthesized.

The in-vitro effect on prostacyclin ($PGI_2$) synthetase is measured analogous to the method of Sun et al., Prostaglandins 14, 1055 (1977);

The testing procedure is as follows:

$^{14}$C-Arachidonic acid is incubated with an enzyme mixture consisting of solubilized and partially purified prostaglandin cyclo-oxygenase from sheep seminal vesicles and crude $PGI_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al. The radioactive zones are located with a scanner; those corresponding to 6-keto-$PGF_1\alpha$ (a stable end product of prostacyclin biotrasformation) and $PGE_2$ are transferred to liquid scintillation vials and counted. The ratio of counts for 6-keto-PGF$_1\alpha$/PGE$_2$ is calculated for each concentration of test compound used. IC$_{50}$ values for inhibition are determined graphically as the concentration of test compound at which the ratio of 6-keto-PGF$_1\alpha$/PGE$_2$ is reduced to 50% of the control value.

The inhibition of the synthesis and the reduction of plasma levels of thromboxane is determined in vivo or administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane B$_2$ and another aliquot for 6-keto-PGF$_1\alpha$ (the stable metabolite of prostacyclin, by radioimmunoassay.

Compounds of the formula I are potent and selective thromboxane synthetase inhibitors. At and above the effective dose levels for thromboxane synthetase inhibition neither the beneficial prostacyclin synthetase enzyme system nor the prostaglandin cyclooxygenase enzyme system is significantly inhibited. Surprisingly, the prostacyclin levels are significantly increased.

The IC$_{50}$ for, e.g. 5-[4-(5-tetrazolyl)-butyl]imidazol[1,5-a]pyridine, and 5-(hydroxycarbamoylpentyl)imidazo[1,5-a]pyridine is about $1 \times 10^{-8}$M and $3 \times 10^{-7}$M respectively for thromboxane synthetase inhibition.

Also further illustrative of the invention, e.g. 5-[4-(5-tetrazolyl)-butyl]imidazo[1,5-a]pyridine reduces the plasma concentration of thromboxane B$_2$ in the rat by over 50% at an oral dose of 5 mg/Kg or lower. A significant increase in the plasma level of the prostacylin metabolite 6-keto-PGF, $\alpha$ is also observed.

The aforementioned advantageous properties render the compounds of this invention of great value as specific therapeutic agents for mammals, e.g. for the treatment of cardiovascular diseases, such as thromboembolism.

The compounds of formula I are prepared advantageously by derivatizing compounds of formula IV

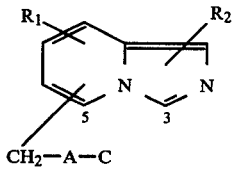

or 5,6,7,8-tetrahydro derivatives thereof wherein R$_1$, R$_2$ and A are as previously defined and C represents carboxy, lower alkoxycarbonyl, carbamoyl or cyano.

Useful as starting materials are the reactive functional derivatives of compounds of formula IV wherein C represents carboxy, preferably acid halides, simple or mixed anhydrides, such as the acid chloride, the acid anhydride (R$_2$″CO)$_2$O, or a mixed anhydride derived from a lower alkoxycarbonyl halide, such as ethyl chloroformate, or from a hindered lower alkanoyl halide, e.g., from pivaloyl chloride, by methods well-known to the art.

The novel intermediates of formula IV—wherein R$_1$ is hydroxy, lower alkoxy or aryl-lower alkoxy, preferably methoxy or benzyloxy; R$_2$ is hydrogen or lower alkyl; A is straight chain or branched alkylene of 2 to 12 carbon atoms (preferably 3 to 8 carbon atoms), alkynylene or alkenylene of 2 to 12 carbon atoms (preferably 4 to 8 carbon atoms) each; C is carboxy, lower alkoxycarbonyl, carbamoyl or cyano (preferably carboxy); and salts thereof—are also active as thromboxane synthetase inhibitors.

Illustrative thereof, 5-(5-carboxypentyl)-6-benzyloxyimidazo[1,5-a]pyridine has an IC$_{50}$ of about $3 \times 10^{-9}$M for thromboxane synthetase inhibition.

The compounds of formula I, wherein B represents 4,5-dihydro-2-oxazolyl or 4,5-dihydro-2-oxazolyl substituted by lower alkyl, are preferably prepared by condensing a compound of formula IV, wherein C represents carboxy or a reactive functional derivative thereof, lower alkoxycarbonyl or carbamoyl, with 2-hydroxy-ethylamine optionally mono-m or di-(vicinal or gem)-C-substituted by lower alkyl, or with aziridine optionally mono- or di-(vicinal or gem)-C-substituted by lower alkyl, e.g. 2-aminoethanol, 2-methyl-2-aminopropanol, 2,2-dimethylaziridine.

The condensation is carried out according to methods generally known per se, e.g. as desribed in J. Organic Chemistry 39, 2787 (1974), preferably in an inert solvent such as toluene at a temperature range of about 25°–100°, and as illustrated herein in the examples.

Said condensation occurs either spontaneously or in the presence of condensing agents, e.g. disubstituted carbodiimides, such as dicyclohexylcarbodiimide, e.g. in the case where C represents carboxy.

The compounds of formula I wherein B represents hydroxycarbamoyl (hydroxamic acids) are preferably prepared by condensing a compound of formula IV, wherein C represents carboxy or a reactive functional derivative thereof, lower alkoxycarbonyl or carbamoyl, with hydroxylamine or an acid addition salt thereof in the presence of a basic reagent, e.g sodium hydroxide.

Said condensation is carried out according to methods known per se. as described in Barton et al., Comprehensive Organic Chemistry, Vol. 2 pp. 1037–1038 (1079), preferably under basic conditions advantageously with hydroxylamine hydrochloride, in an inert polar solvent, e.g. a lower alkanol such as ethanol, preferably at a temperature range of about 0° to 50°, advantageously at room temperature.

The compounds of formula I wherein B represents 5-tetrazolyl are preferably prepared by condensing a compound of formula IV, wherein C represents preferably cyano, with hydroazoic acid or a compound which serves as a source of hydrazoic acid, e.g. a metal or ammonium salt of hydrazoic acid, preferably an alkali metal azide such as sodium azide or ammonium azide.

Said condensation is carried out according to methods known per se, e.g. as described in Barton et al, Comprehensive Organic Chemistry Vol. 4. pp 407–409 (1979), preferably in a solvent such as dimethylformamide and at an elevated temperature ranging from about 50° to 200°, advantageously 75° to 150°, and in the presence of an acid, e.g. hydrochloric acid or ammonium chloride.

Said tetrazoles may also be prepared from a compound of formula IV wherein C representing cyano or carbamoyl is first converted to (halo or lower alkoxy)-iminocarbonyl for condensation with e.g. an alkali metal azide or ammonium azide.

The starting materials of formula IV can be prepared as follows:

(a) condensing a compound of the formula VI

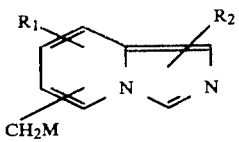

wherein M is an alkali metal; R₁ represents hydrogen, lower alkyl, lower alkoxy or aryl-lower alkoxy; R₂ is hydrogen or lower alkyl; with a reactive functional derivative of a compound of the formula VII

HO-A-C'  (VII)

wherein A is straight chain or branched alkylene of 1 to 12 carbon atoms, alkynylene or alkenylene of 2 to 12 carbon atoms; C' represents carboxy, trialkoxymethyl, carbamoyl, cyano, or halomethyl; to yield a compound of formula IVa.

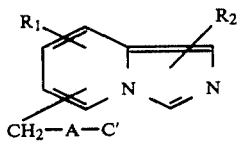

wherein A, C', R₁ and R₂ have meaning given above; and converting any resulting product wherein C' differs from C, into a compound of formula IV;

Reactive organometallic compounds of formula VI wherein M is an alkali metal are obtained by metallation of the appropriate methyl substituted imidazo[1,5-a]pyridine, e.g. 5-methylimidazo[1,5-a]pyridine, prepared as described in the Journal of Organic Chemistry 40, 1210 (1975), with a reactive metallating agent, e.g. butyl lithium or lithium diisopropylamide in an inert solvent such as tetrahydrofuran at a temperature below room temperature, preferably at about −50°.

Condensation of the intermediate of formula VI with reactive functional derivatives of a compound of formula VII proceeds at a temperature range preferably from about −75° to +50°. In the case where C' represents carboxy the appropriate metal salt, e.g. the lithium salt, of the reactive functional derivative of the corresponding compound of formula VII is first prepared for the condensation with intermediate VI.

Alternately the starting materials of formula IV can also be prepared as follows:

(b) Condensing a compound of formula VIII

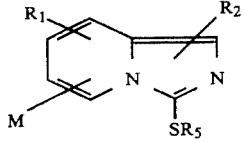

wherein M is an alkali metal, R₁ and R₂ having meaning given above, R₅ is lower alkyl with a reactive functional derivative of a compound of the formula IX

HOCH₂—A—C'  (IX)

wherein A is straight chain or branched alkylene of 1 to 12 carbon atoms alkynylene or alkenylene of 2 to 12 carbon atoms; C' represents carboxy, trialkoxymethyl, carbamoyl, cyano, or halomethyl; converting any resulting product wherein C' differs from C into a compound with a group C; and desulfurizing the resulting compound.

Preparation of the organometallic intermediate VIII and subsequent condensations are carried out as described supra and in Tetrahedron Letters 21, 2195-6 (1980). Desulfurization is preferably performed with a desulfurization catalyst such as Raney nickel in a solvent such as ethanol, preferably at elevated temperature;

(c) condensing under basic catalysis a compound of the formula X

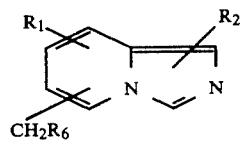

wherein R₁ and R₂ are as previously defined; and R₆ represents lower alkoxycarbonyl or cyano; with a reactive functional derivative of a compound of the formula VII

HO—A—C'  (VII)

wherein A is straight chain or branched alkylene of 1 to 12 carbon atoms, alkynylene or alkenylene of 2 to 12 carbon atoms; C' represents carboxy, trialkoxymethyl, carbamoyl, cyano, or halomethyl; hydrolyzing, decarboxylating the resulting product; converting any resulting compound wherein C' differs from C into a compound of formula IV.

The intermediates of formula X are prepared from the compound of formula VI supra on treatment with e.g. carbon dioxide and esterifying the resulting carboxylic acid, or with a di-(lower)alkyl carbonate or with a cyanogen halide.

(d) cyclizing a compound of formula XI

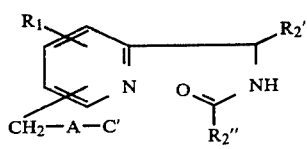

wherein R₁ has meaning as previously described, R₂' and R₂'' represent hydrogen or lower alkyl; A has meaning given above; and C' represents carboxy, lower alkoxycarbonyl, carbamoyl, cyano, or halomethyl; to yield a compound of formula IVa; converting any resulting compound wherein C' differs from C into a compound of formula IV.

The cyclization of the amides of formula XI is advantageously carried out under conditions such as described for the cyclization of 6-methyl-2-methylaminopyridine to 5-methylimidazo[1,5-a]pyridine in J. Org. Chemistry 40, 1210(1975). Said cyclization may be achieved advantageously with a Lewis acid, such as polyphosphoric acid, phosphorous oxychloride, polyphosphate ester, optionally in an inert solvent such as toluene, at a temperature range of 25° to 150°, preferably 50° to 120° C.

The amides of formula XI are prepared by acylating a compound of formula XII

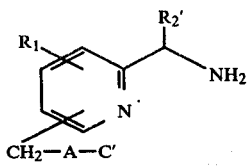

(XII)

wherein $R_1$, $R_2'$, A and C' have meaning given above, with a carboxylic acid of the formula XIII, $R_2''COOH$ (XIII)

wherein $R_2''$ has meaning given above, or with a reactive functional derivative thereof.

Reactive functional derivatives of compounds XIII are preferably acid halides, simple or mixed anhydrides, such as the acid chloride, the acid anhydride $(R_2''CO)_2O$, or a mixed anhydride derived from a lower alkoxycarbonyl halide, such as ethyl chloroformate, or from a hindered lower alkanoyl halide, e.g., from pivaloyl chloride, by methods well-known to the art.

Said condensation of compounds XII and XIII (the acylation of XII) occurs either spontaneously by e.g. heating with formic acid, or in the presence of condensing agents, e.g. disubstituted carbodiimides, such as dicyclohexylcarbodiimide.

The acylation of compounds of formula XII with a reactive functional derivative of XIII, e.g. acetyl chloride or acetic anhydride, occurs advantageously in the presence of an organic or inorganic base, e.g., potassium carbonate, triethylamine.

The amines of formula XII may be obtained, e.g. from the correspondingly substituted 2-(cyano, or lower hydroxyiminoalkyl)pyridines by reduction, e.g. by hydrogenation in the presence of a catalyst such as palladium on charcoal or by treatment with a chemical reducing agent such as borane or sodium cyanoborohydride, the reducing agent being chosen according to the type of other functional groups present in the molecule. The compounds of formula XII may also be obtained by amination of the correspondingly substituted and reactively esterified 2-(hydroxymethyl)pyridines.

Certain terms used in the foregoing processes have the meanings as defined below.

Reactive functional derivatives of alcohols of formula VII and IX are e.g. such esterified by a strong inorganic or organic sulfonic acid above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)methyl, particularly triethoxy- or trimethoxymethyl.

Halomethyl represents especially chloromethyl but may also be bromometnhyl or iodomethyl.

An alkali metal represents preferably lithium but may also be potassium or sodium.

Hydrolysis of intermediates wherein C' represents trialkoxymethyl to compounds of formula IV wherein C is carboxy is advantageously carried out with inorganic acids such as a hydrohalic or sulfuric acid.

Intermediates, e.g. of formula IVa wherein C' is halomethyl may be reacted preferably with a metal cyanide such as potassium cyanide in a conventional manner to yield the compounds of formula IV wherein the chain is extended by 1 carbon atom and C is cyano. These in turn are converted to compounds of formula IV wherein C is carboxy or alkoxycarbonyl using methods known to the art.

Thus, the compounds of formula IV wherein C represents cyano (nitriles) are converted to compounds of formula IV wherein C is carboxy by hydrolysis with inorganic acids e.g. a hydrohalic acid such as hydrochloric acid or sulfuric acid in aqueous solution, or advantageously by hydrolysis with aqueous alkali metal hydroxide e.g. potassium hydroxide at reflux temperature.

The conversion of said nitriles to compounds of formula IV wherein C represents lower alkoxycarbonyl is advantageously carried out by treatment first with a lower alkanol, e.g. anhydrous ethanol, in the presence of a strong acid, e.g. hydrochloric acid preferably at reflux temperature, followed by careful hydrolysis with water.

Furthermore, the intermediates, e.g. of formula IVa, wherein C' is halomethyl, such as chloromethyl, are converted to compounds of formula IV, wherein C is carboxy and the chain length is extended by two carbons, by first treating with e.g. a di-(lower)alkyl malonate, such as diethyl malonate, in the presence of a base such as potassium carbonate or sodium ethoxide, in a solvent such as dimethylformamide, preferably at a temperature range from 50° to 100°. The resulting substituted di(lower)alkyl malonate is hydrolyzed, advantageously with aqueous base, such as dilute sodium hydroxide, to the corresponding malonic acid which is decarboxylated under standard conditions, e.g. by heating in xylene solution, to give a compound of formula IV wherein C is carboxy. Substitution of the di-(lower)alkyl malonate with a lower alkyl cyanoacetate yields the corresponding compounds of formula IV wherein C is cyano.

Intermediates of formula IV wherein A represents straight chain or branched alkenylene with a terminal double bond, may also be prepared from intermediates of formula IVa wherein C' is halomethyl. For instance, said intermediates are first treated with e.g. a lower alkyl ester of an α-(aryl- or alkylthio)-acetic acid such as ethyl α-(phenylthio)-acetate, in the presence of a strong base such as sodium hydride. Subsequent oxidation of the resulting α-arylthio or α-alkylthio substituted ester to the α-arylsulfinyl or α-alkylsulfinyl ester with e.g. sodium periodate, followed by heat-induced elimination, by e.g. refluxing in xylene, yields a compound of general formula IV (an α,β-unsaturated ester) wherein A represents alkenylene and C represents e.g. lower alkoxycarbonyl, and the chain length has been extended by two carbon atoms. Similarly, the compounds, e.g. of formula IVa, wherein C' represents halomethyl may first be converted to the corresponding carboxaldehydes with e.g. dimethylsulfoxide in the presence of triethylamine and silver tetrafluoroborate. Subsequent Wittig condensation e.g. with ethyl (triphenylphosphoranylidene)-acetate also yields the above-cited α,β-unsaturated esters.

The compounds of formula IV wherein C represents unsubstituted carbamoyl may be dehydrated to the corresponding nitriles by treatment with e.g. phosphorus oxychloride or thionyl chloride in an inert solvent such as toluene.

Free carboxylic acids may be esterified with lower alkanols such as ethanol in the presence of a strong and e.g. sulfuric acid advantageously at elevated temperature or with diazo (lower) alkanes, e.g. diazomethane in a solvent such as ethyl ether, advantageously at room temperature, to give the corresponding esters, namely compounds of formula IV wherein C is lower alkoxycarbonyl.

The compounds of formula I may also be prepared in a fashion analogous to the methods (a), (b), (c) and (d) described for the preparation of the intermediates of formula IV. For said processes the starting materials correspond to the compounds of formula VII, IX, XI and XII in which the group C' is replaced by group B representing 5-tetrazolyl, hydroxycarbamoyl, 4,5-dihydro-2-oxazolyl or 4,5-dihydro-2-oxazolyl substituted by lower alkyl.

Compounds of formula I wherein A represents alkylene may be converted to the corresponding 5,6,7,8-tetrahydroimidazo[1,5-a]pyridine compounds by reduction with hydrogen in the presence of a hydrogenation catalyst, e.g. palladium, and an acid e.g. a mineral acid, for instance hydrochloric acid in an inert solvent, e.g. ethanol.

Furthermore compounds of formula I wherein A represents a straight chain or branched alkynylene or alkenylene may be converted by catalytic hydrogenation, advantageously under neutral conditions e.g,. with palladium catalyst at atmospheric pressure in an inert solvent, e.g. ethanol, to compounds of formula I wherein A represents straight chain or branched alkylene.

Compounds of formula I or IV wherein $R_1$ is e.g. benzyloxy or methoxy can be converted to compounds of formula I or IV wherein $R_1$ is hydroxy by e.g. hydrolysis or hydrogenolysis by methods well-known to the art.

Furthermore compounds of formula I wherein $R_1$ and $R_2$ represent hydrogen can be converted to the corresponding halo derivatives by direct halogenation with chlorine, bromine or iodine.

The above-mentioned reactions are carried out according to standard methods, in the presence or absence of diluents, preferably such as are inert to the reagents and are solvents thereof, of catalysts, condensing or said other agents respectively, and/or inert atmospheres, at low temperatures, room temperature or elevated temperatures, preferably at the boiling point of the solvents used, at atmospheric or superatmospheric pressure, and with temporary protection of reactive groups as required.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of isomers, such as racemates, mixtures of diastereoisomers, mixtures of racemates or mixtures of geometrical isomers.

Resulting mixtures of diastereoisomers, mixtures of racemates and geometric isomers can be separated on the basis of the physicochemical differences of the constituents, in known manner, into the pure isomers, diastereoisomers, racemates, or geometric isomers for example by chromatography and/or fractional crystallisation.

Resulting racemates can furthermore be resolved into the optical antipodes by known methods, for example by recrystallisation from an optically active solvent, by means of microorganisms or by reacting an acidic end product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereomeric salts thereof, e.g. by the fractional crystallization of d- or l-tartrates.

Advantageously, the more active of the two antipodes is isolated.

Finally, the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents 5-tetrazolyl or hydroxycarbamoyl can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for the crystallisation.

The pharmaceutical compositions according to the invention are those suitable for enteral, such as oral or rectal, and parenteral administration to mammals, including man, for the treatment or prevention of diseases responsive to inhibition of thromboxane synthetase such as peripheral vascular diseases, comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 20 to 200 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg. Examples 1 to 28 are directed to representative starting materials, e.g. of formula IV and IVa.

EXAMPLE 1

To a solution of 50 g of 5-methylimidazo[1,5-a]pyridine [J. Org. Chem. 40, 1210 (1975)] in 625 ml of tetrahydrofuran precooled to −75° is added under nitrogen atmosphere 175 ml of 2.4N n-butyllithium in hexane while maintaining temperature below −53°. The solution of 5-(lithiomethyl)imidazo[1,5-a]pyridine, is cooled back to −75° and a solution of 121.8 g of 5-bromo-1,1,1-triethoxypentane in 125 ml of tetrahydrofuran is added rapidly at which time the temperature rises to −60°. The reaction mixture is allowed to warm to −4° over a 45 minute period and evaporated practically to dryness. The residue is partitioned between 500 ml of ethyl ether and 240 ml of 3N hydrochloric acid. The ether solution is further extracted twice with 60 ml of 3N hydrochloric acid; the combined aqueous extract is basified with 100 ml of concentrated ammonia hydroxide and reextracted twice with 200 ml of ethyl ether. The ether extract is dried over magnesium sulfate and evaporated to dryness to give an oil which is distilled under high vacuum to give 5-(5-ethoxycarbonylpentyl)-imidazo[1,5-a]pyridine boiling at 180°–5°/0.12 mm Hg.

EXAMPLE 2

A suspension of 26 g of 5-(5-ethoxycarbonylpentyl)imidazo[1,5-a]pyridine in 100 ml of 1N aqueos sodium hydroxide solution is heated on a steam bath for two hours; 10 ml of ethanol is added and heating is continued for 45 minutes. The reaction mixture is cooled, washed with 300 ml of ether and the solution is adjusted to pH 5.5 with concentrated hydrochloric acid. The crystallized product is collected by filtration and washed with 50 ml of water to yield 5-(5-carboxypentyl)-imidazo[1,5-a]pyridine melting at 144°–7°.

EXAMPLE 3

(a) To a solution of 39.6 g of 5-bromovaleric acid in 400 ml of tetrahydrofuran cooled to −78° is added slowly 93 ml of 2.3N n-butyl lithium solution in hexane so as to maintain the temperature below −65°. The suspension is stirred for 20 minutes. Then a solution of 5-(lithiomethyl)imidazo[1,5-a]pyridine, prepared from 26.9 g of 5-methylimidazo[1,5-a]pyridine and 93 ml of 2.3N n-butyl lithium solution as described in example 1, is added all at once at −75°. The reaction mixture is stirred at −75° for two hours, allowed to warm to room temperature, treated with 15 ml of 12N hydrochloric acid, and evaporated under vacuum.

The residue is partitioned between water and methylene chloride after pH is adjusted to 10. The aqueous solution is further washed with chloroform, acidified to pH 1 and again washed with ether and toluene. After pH is adjusted to 5.5, extraction with chloroform gives crude 5-(5-carboxypentyl)imidazo-[1,5-a]pyridine. A solution of the acid in 30 ml of acetonitrile is treated with 5N ethanolic hydrochloric acid. After addition of 25 ml of ethyl ether, 5-(5-carboxypentyl)imidazo[1,5-a]pyridine hydrochloride, melting at 201°–4°, crystallizes. 5-(5-Carboxypentyl)-imidazo[1,5-a]pyridine (example 2) is obtained on neutralization of a methanolic solution of the salt to pH 5.

(b) Similarly prepared from 6-bromohexanoic acid is 5-(6-carboxyhexyl)-imidazo[1,5-a]pyridine melting at 137°–9°.

(c) 5-(7-carboxyheptyl)-imidazo[1,5-a]pyridine melting at 97°–101° is similarly prepared from 7-bromoheptanoic acid.

EXAMPLE 4

A solution of 37 g of 5-(5-chloropentyl)-imidazo[1,5-a]pyridine, 21.7 g of potassium cyanide and 3 g of dibenzo-18-crown-6 in acetonitrile is heated under reflux for 20 hours. The acetonitrile is evaporated under reduced pressure, the residue is partitioned between water and methylene chloride, and the methylene chloride extract is evaporated to dryness. Treatment of a solution of the residue in ether with ethanolic hydrochloric acid yields 5-(5-cyanopentyl)-imidazo[1,5-a]pyridine hydrochloride melting at 178°–80°.

The starting material is prepared as follows:

A solution of 30 g of 1-bromo-4-chlorobutane in 20 ml of dry tetrahydrofuran is added to a solution of 5-(lithiomethyl)imidazo[1,5-a]pyridine (prepared from 22 g of 5-methylimidazo[1,5-a]pyridine and 80 ml of 2.3N solution of n-butyl lithium in hexane according to example 1) while maintaining the temperature below −50°. The reaction mixture is stirred for 2 to 3 hours at −50°, allowed to warm to room temperature, stirred overnight, and evaporated to dryness.

The solution of the residue in methylene chloride is washed with water, dried over magnesium sulfate and evaporated to dryness to give the 5-(5-chloropentyl)-imidazo[1,5-a]pyridine which is used without further purification.

EXAMPLE 5

5-(4-chlorobutyl)-imidazo[1,5-a]pyridine is converted in a manner anologous to that described for Example 4, to 5-(4-cyanobutyl)-imidazo[1,5-a]pyridine melting at 72°–77°.

EXAMPLE 6

By a procedure analogous to that described for example 4, 3,5-dimethylimidazo[1,5-a]pyridine [J. Het. Chem. 3,33 (1966)] is converted to 5-(5-chloropentyl)-3-methyl-imidazo[1,5-a]pyridine, melting at 98°–104°. Reaction with potassium cyanide, under the conditions of example 4, and treatment with ethanolic hydrogen bromide yields the 5-(5-cyanopentyl)-3-methylimidazo[1,5-a]pyridine hydrobromide melting at 215°–220°.

EXAMPLE 7

A solution of 36 g of 5-(cyanopentyl)-imidazo[1,5-a]pyridine in 100 ml of methanol and 50 ml of 45% aqueous potassium hydroxide solution is heated under reflux for 48 hours. The methanol is removed by evaporation under reduced pressure, and water is added. The basic solution is washed with ethyl acetate and acifified to pH 5.5-6 with concentrated hydrochloric acid.

The crystallized acid is collected, and recrystallized from ethanol to yield the product of example 2, namely the 5-(5-carboxypentyl)-imidazo[1,5-a]pyridine melting at 142°–5°, further recrystallization raises the melting point to 144°–7°.

EXAMPLE 8

Hydrolysis of 5-(4-cyanobutyl)-imidazo[1,5-a]pyridine as described for example 7 yields 5-(4-carboxybutyl)-imidazo[1,5-a]pyridine melting at 161°–3°.

EXAMPLE 9

Hydrolysis as described for example 7, of 5-(5-cyanopentyl)-3-methyl-imidazo[1,5-a]pyridine yields 5-(5-carboxypentyl)-3-methyl-imidazo[1,5-a]pyridine melting at 170°–3°.

EXAMPLE 10

To a solution of 3 g of 5-(5-cyanopentyl)-3-methyl-imidazo[1,5-a]pyridine hydrochloride in a mixture of 20 ml of ethanol and 5 ml of 1N sodium hydroxide solution is added 10 ml of 30% hydrogen peroxide solution; 5 ml of ethanol and a sufficient volume of 1N sodium hydroxide solution to reach pH 10 are then added.

After stirring at room temperature overnight, the ethanol is evaporated under reduced pressure, water is added and the mixture is extracted with methylene chloride. The resulting product is crystallized from ether and recrystallized from acetonitrile to yield 5-(5-carbamoylpentyl)-imidazo[1,5-a]pyridine melting at 131°–2°.

EXAMPLE 11

(a) A solution of 2.7 g of 5-(6-carboxyhexyl)-imidazo[1,5-a]pyridine in a mixture of 120 ml of ethanol and 30 ml of concentrated hydrochloric acid is hydrogenated at 3 atmospheres in the presence of 1 g of 10% palladium on charcoal catalyst until 2 moles of hydrogen are consumed. The mixture is filtered free of catalyst and evaporated to dryness. The residue is recrystallized from isopropanol-ether to yield the 5-(6-carboxyhexyl)-5,6,7,8-tetrahydroimidazo[1,5-a]pyridine hydrochloride melting at 150°–4°.

(b) Similar hydrogenation of 5-(5-carboxypentyl)-imidazo[1,5-a]-pyridine yields 5-(5-carboxypentyl)-5,6,7,8-tetrahydroimidazo[1,5-a]pyridine hydrochloride melting at 146°–50°.

(c) Similar hydrogenation of 5-(4-carboxybutyl)-imidazo[1,5-a]pyridine yields 5-(4-carboxybutyl)-5,6,7,8-tetrahydroimidazo[1,5-a]pyridine hydrochloride melting at 120°–3°.

EXAMPLE 12

A solution of 2.3 g (0.011 mole) of 5-bromo-3,3-dimethylpentanoic acid [J. Org. Chem. 44, 1258 (1979)] in 20 ml of dry tetrahydrofuran is cooled to −70° under nitrogen, 5.05 ml of 2.4M n-butyllithium in hexane is added dropwise. After addition is complete the solution of 5-(lithiomethyl)-imidazo[1,5-a]pyridine in hexane (prepared from 1.32 g of 5-methylimidazo-[1,5-a]pyridine and 5.05 ml of 2.4N n-butyllithium in hexane) is added all at once. The mixture is stirred at room temperature overnight.

The reaction mixture is diluted with water, sodium carbonate is added and the basic solution is then extracted 3 times with chloroform. The aqueous phase is washed 3 times with ether after acidification to pH 2. Finally the aqueous phase is adjusted to pH 5 and extracted with ethyl acetate/ether. The extracts are dried and evaporated to give a yellow oil. Material is crystallized from ethanol/ether to give 5-(5-carboxy-4,4-dimethylpentyl)-imidazo[1,5-a]pyridine, melting at 124°–9°.

EXAMPLE 13

Iodine crystals (1.9 g) are added to a well-stirred solution of 1.16 g of 5-(5-carboxymethyl)-imidazo[1,5-a]pyridine and 1.68 g of sodium bicarbonate in 10 ml of water and 1 ml of ethanol. Additional 4 ml of ethanol are added to dissolve the bulk of the iodine and stirring is continued for 45 minutes. The reaction mixture is diluted with 125 ml of water and extracted twice with methylene chloride at pH 8 (NaHCO$_3$ added if necessary). The aqueous phase is concentrated in vacuo, charcoaled and adjusted to pH 4.5 with 2N HCl. The precipitate is collected, dried and recrystallized from methanol/ether to give 1-iodo-5-(5-carboxypentyl)-imidazo[1,5-a]pyridine melting at 163°–165°.

EXAMPLE 14

A solution of 5-methylimidazo[1,5-a]pyridine (4.0 g) and tetramethylethylene diamine (4.9 g) in 100 ml of tetrahydrofuran is cooled to 0° under nitrogen and 26.5 ml of 1.6N n-butyllithium is hexane is added dropwise maintaining the temperature below 2°. After 30 minutes this solution is transferred under nitrogen over 45 minutes to an ice-cold solution of 5-bromovalerontrile (4.86 g) in 80 ml of tetrahydrofuran. After 15 minutes the solvent is evaporated and the residue is partitioned between water and ethyl acetate. The organic phase is reextracted with 2N hydrochloric acid (3×15 ml). Basification of the aqueous phase to pH=10 with 50% sodium hydroxide, extraction with ethyl acetate (2×75 ml), drying over magnesium sulfate, evaporation and chromatography (SiO$_2$, ethyl acetate) yields 5-(5-cyanopentyl)-imidazo[1,5-a]pyridine.

EXAMPLE 15

To a solution of 4 g of 5-(4-ethoxycarbonylbutyl)-3-ethylthio-imidazo[1,5-a]pyridine in 100 ml of ethanol is added approximately 5 g of Raney nickel. The solution is heated under reflux for 18 hours. The Raney Nickel is removed by filtration and the filter cake washed with 100 ml of ethyl acetate. The filtrate is evaporated to dryness under reduced pressure to yield the product as a heavy oil. This material is purified by column chromatography on silica gel using an ether-hexane mixture (1:3) as eluent. Evaporation of the solvent under reduced pressure yields 5-(4-ethoxycarbonylbutyl)imidazo[1,5-a]pyridine as a yellow oil; NMR (CDCl$_3$) 1.25 (t, 3H), 4.15 (q, 2H), 8.1 (s, 1H).

The starting material is prepared as follows:

A solution of 17.8 g of 3-ethylthio-imidazo[1,5-a]pyridine in 200 ml of tetrahydrofuran (dried) is cooled to −70°, and 80 ml of 1.6M n-butyl lithium in hexane is added dropwise to the stirred solution over a period of 15 minutes. On completion of the addition, the reaction is allowed to stir at −70° for a further 30 minutes. To the reaction mixture is added dropwise a solution of 20 g of ethyl 4-bromopentanoate in 75 ml of tetrahydrofuran. The reaction mixture is allowed to warm up to −10° where it is maintained for 30 minutes and subsequently is allowed to stand for 1 hour at room temperature. To the reaction mixture is added 400 ml of diethyl ether and 400 ml of 4N hydrochloric acid. The aqueous layer is separated and the ethereal layer is washed with water. The combined aqueous extracts are rendered basic with ammonium hydroxide and extracted with 3×200 ml of ether. The ethereal extract is dried over anhydrous magnesium sulfate and the solvent evaporated under reduced pressure to yield the crude product as a heavy oil. This material is purified by column chromatography on silica gel using a 4:1 mixture of pentane-diethyl ether as eluent. On evaporation of the solvent the product was distilled to give 3-ethylthio-5-(5-ethoxycarbonylbutyl)imidazo[1,5-a]pyridine, boiling at 170°/0.3 mm Hg; NMR (CDCl$_3$) 1.25 (t,3H), 1.30 (t,3H), 3.15 (q,2H), 4.15 (q,2H).

EXAMPLE 16

A solution of 3 g of 5-[5-ethoxycarbonyl-5-(phenylsulfinyl)pentyl]-imidazo[1,5,-a]pyridine in 50 ml xylene is heated at reflux temperature for 30 minutes under an atmosphere of nitrogen. The xylene is then removed by distillation under reduced pressure, the residue is dissolved in 15 ml of diethyl ether and purified by column chromatography on silica gel. The product is eluted using a 2:1 mixture of diethyl ether and ethyl acetate as eluent. Evaporation of the solvent yields 5-(5-ethoxycarbonylpent-4-enyl)-imidazo[1,5-a]pyridine as an oil; NMR (CDCl$_3$) 1.29 (t,3H), 4.25 (q,2H), 5.88 (d, 1H).

The starting material is prepared as follows:

To an ice-cooled, magnetically stirred slurry of 0.96 g of sodium hydride in 50 ml dimethylformamide is added 3.92 g of ethyl 2-(phenylthio)acetate in a dropwise manner over a period of 15 minutes. The suspension is stirred at room temperature for 2 hours and then cooled to 5° by means of an ice-bath. To this suspension is added 4.16 g of 5-(4-chlorobutyl)-imidazo[1,5-a]pyridine in a dropwise manner over a period of 1 hour. On completion of the addition, 3.2 g of sodium iodide is added to the reaction mixture which is then allowed to stir overnight at room temperature.

The reaction mixture is poured into 150 ml of ice water and extracted with 3×100 ml aliquots of a 1:1 mixture of diethyl ether and ethyl acetate. The organic phase is washed with 2×100 ml of brine and then extracted with 3×50 ml portions of 1N hydrochloric acid. The acidic aqueous extracts are combined, basified with ammonium hydroxide and extracted with 3×150 ml portions of a 1:1 mixture of diethyl ether and ethyl aetate. These organic extracts are dried over anhydrous magnesium sulfate, filtered and the solvent concentrated under reduced pressure to yield the product as an oil, which is purified by column chromatography on silica gel using diethyl ether as eluent. Evaporation of the solvent yields 5-[5-ethoxycarbonyl-5-(phenylthio)pentyl]-imidazo[1,5-a]pyridine as a heavy oil; NMR (CDCl$_3$) 3.3–3.8 (1H); IR 1720 cm$^{-1}$.

To a solution of 3.8 g of 5-[5-ethoxycarbonyl-5-(phenylthio)pentyl]-imidazo[1,5-a]pyridine in 100 ml of methanol is added 2.8 g of sodium metaperiodate. The reaction mixture is allowed to stir at room temperature for 18 hours. The solvent is evaporated under reduced pressure and 150 ml of water is added to the residue, which is extracted with 3×100 ml of ethyl acetate. The organic phase is extracted with 2×500 ml portions of 1N hydrochloric acid followed by basification of the aqueous extract with ammonium hydroxide and re-extraction into 2×100 ml portions of ethyl acetate. These combined ethyl acetate extracts are dried over anhydrous magnesium sulfate, filtered and the solvent concentrated under reduced pressure to yield an oil which is purified by column chromatography on silica gel using ethyl acetate, diethyl ether (1:1) as eluent. Evaporation of the solvent yields 5-[5-ethoxycarbonyl-5-(phenylfulfinyl)pentyl]-imidazo[1,5-a]pyridine as an oil; IR 1720 cm$^{-1}$, 1040 cm$^{-1}$.

EXAMPLE 17

To a solution of 300 mg of 5-(5-ethoxycarbonylpent-4-enyl)-imidazo[1,5a]pyridine in 20 ml methanol is added 5 ml of 1N sodium hydroxide. The reaction mixture is stirred at room temperature for 18 hours. The methanol is evaporated under reduced pressure and an additional 5 ml of water is added to the aqueous residue, which is then extracted with 3×5 ml aliquots of ethyl acetate. The basic aqueous layer is then adjusted to pH 5 and extracted with 3×5 ml portions of ethyl acetate. These extracts are dried over anhydrous magnesium sulfate, filtered and the solvent evaporated under reduced pressure to yield 5-(5-carboxypent-4-enyl)-imidazo[1,5-a]pyridine melting at 142°–144°.

EXAMPLE 18

To a solution of 2.75 g of 5-(5-formylpentyl)-imidazo[1,5-a]pyridine in 180 ml of chloroform is added 6.5 g of carbethoxymethylene-triphenylphosphorane. The reaction mixture is stirred at room temperature for 18 hours. The solvent is then evaporated under reduced pressure to yield 5-(7ethoxycarbonyl-hept-6-enyl-imidazo[1,5-a]pyridine as an oil.

The starting material is prepared as follows:

To a cooled (−60°) solution of 4.9 g of 5-(5-methoxycarbonylpentyl)-imdiazo[1,5-a]pyridine (obtained by esterification of 5-(5-carboxypentyl)-imidazo[1,5-a]pyridine of Example 2 with diazomethane in methylene chloride) in 140 ml of methylene chloride is added 40 ml of a 1.75M solution of di-isobutyl aluminum hydride in hexane in a dropwise manner over a 20 minute period. On completion of the addition, the reaction is allowed to stir at −60° for a further 20 minutes. Then, 10 ml of methanol, followed by 100 ml of water, are added to quench the reaction. The reaction mixture is stirred at room temperature for 15 minutes, the methylene chloride layer is separated and the solvent evaporated under reduced pressure to yield 5-(5-formylpentyl)-imidazo[1,5-a]pyridine as an oil; NMR (CDCl$_3$) 9.7 (m, 1H); IR (CH$_2$Cl$_2$) 1710 cm$^{-1}$.

EXAMPLE 19

To a solution of 2.8 g of 5-(7-ethoxycarbonyl-hept-6-enyl)imidazo[1,5-]pyridine in 30 ml of methanol is added 15 ml of 1N sodium hydroxide. The reaction is stirred at room temperature for 3 hours. The methanol is evaporated under reduced pressure and the residue diluted with 30 ml of water and the solution adjusted to pH 7 with 1N hydrochloric acid. The solution is extracted with 2×50 ml of ethyl acetate. The combined ethyl acetate extracts are dried over anhydrous magnesium sulfate, filtered and the solvent evaporated under reduced pressure to yield 5-(7-carboxyhept-6-enyl)-imidazo-[1,5-a]yridine melting at 110°–111°.

EXAMPLE 20

A solution of 0.1 g of 2-aminomethyl-3-(4-methoxycarbonylbutyl)pyridine in 0.6 ml of formic acid is heated at 90° for 18 hours. The mixture is cooled to 0°, made basic with saturated ammonium hydroxide solution and extracted with methylene chloride (4×10 ml). Drying, filtration and evaporation of the extracts yields 2-(N-formylaminomethyl)-3-(4-methoxycarbonylbutyl)pyridine, melting at 43°–45° C. which is redissolved in 1 ml of toluene and heated at 90° for 17 hours with 75 mg of phosphorus oxychloride. Evaporation of excess phosphorus oxychloride with toluene, basification at 0° with saturated ammonium hydroxide solution, extraction with methylene chloride (4×15 ml) and drying over sodium sulfate yields an oil, which is chromatographed (silica gel, ethyl acetate) to yield as an oil, 8-(4-methoxycarbonylbutyl)imidazo[1,5-a]pyridine; Rf 0.29;NMR (CDCl$_3$) 3.70 (s, 3H), 6.50 (d, 2H), 7.43 (s, 1H), 7.83 (t, 1H), 8.22 (s, 1H); IR (CH$_2$Cl$_2$) 1725 cm$^{-1}$.

The starting material is prepared as follows:

A solution of 3-bromopyridine (7.9 g), methyl 4-pentenoate (7.15 g), palladium acetate (0.11 g) and tri-o-tolylphosphine (0.6 g) in 50 ml of triethylamine is refluxed for 24 hours under argon and the solvent evaporated. The residue is taken up in methylene chloride (50 ml) and washed with water (2×40 ml). The organic phase is dried and evaporated to yield 3-(4-methoxycarbonylbut-1-enyl)pyridine as a colorless liquid; NMR (CDCl$_3$) 3.72 (s, 3H), 6.40 (s, 1H); IR (film) 1725 cm$^{-1}$.

3-(4-Methoxycarbonylbut-1-enyl)pyridine (9.5 g) is hydrogenated in 100 ml of methanol at 3 atmospheres for 3.5 hours with 0.5 g of 5% palladium on charcoal to yield, after filtration and evaporation, 3-(4-methoxycarbonylbutyl)pyridine as an oil; NMR (CDCl$_3$) 3.80 (s, 3H); IR (CH$_2$Cl$_2$) 1730 cm$^{-1}$.

Peracetic acid (40%, 8.3 ml) is added dropwise to 3-(4-methoxycarbonylbutyl)pyridine (10.81 g) so as to maintain the reaction temperature between 80° and 85°. After the addition is complete, the temperature is allowed to fall to 30° and excess peracid is destroyed with aqueous sodium sulfite. The acetic acid is distilled at reduced pressure, and the residue is taken up in methylene chloride (50 ml), filtered and evaporated. The residue consisting of 3-(4-methoxycarbonylbutyl)pyridine-N-oxide is treated with dimethyl sulfate (7.7 g) in 40 ml of toluene at 90° for 1 hour and the solvent is evaporated. The 3-(4-methoxycarbonylbutyl)-1-methoxypyridinium methyl sulfate salt is dissolved in 16.7 ml of ice-cold water and 8.3 ml of 1N sodium hydroxide, and a solution of potassium cyanide (11.21 g) in 16.7 ml of ice-cold water is added slowly so as to keep the reaction temperature below 0°. After 24 hours at 0°, extraction with methylene chloride (3×30 ml), drying over sodium sulfate and evaporation of solvent yields a mixture of isomeric cyanopyridines from which 2-cyano-3-(4-methoxycarbonylbutyl)pyridine having Rf=0.56 and NMR (CDCl$_3$) 8.52 (m, 1H), and 2-cyano-5-(4-methoxycarbonylbutyl)pyridine having Rf=0.50 and NMR (CDCl$_3$) 8.72 (s, 1H) are separated by chromatography (silica gel, ether-pentane 3:2).

2-Cyano-3-(4-methoxycarbonylbutyl)pyridine (2.40 g) is dissolved in 92 ml of methanol containing 2.4 ml of conc. hydrochloric acid and hydrogenated at atmospheric pressure with 1.2 g of 10% palladium on charcoal for 3 hours. Filtration, evaporation and recrystallization from ether-methylene chloride yields 2-aminomethyl-3-(4-methoxycarbonylbutyl)pyridine hydrochloride, m.p. 79°–81°.

EXAMPLE 21

A solution of 8-(4-methoxycarbonylbutyl)-imidazo[1,5-a]pyridine (30 mg) in 0.3 ml of ethanol and 0.3 ml of 1N sodium hydroxide is refluxed for 2 hours, cooled, diluted with 2 ml of water and extracted with ethyl acetate (1×5 ml). The aqueous phase is brought to pH=6 and is extracted with methylene chloride (4×10 ml). The extracts are dried and evaporated to yield 8-(4-carboxybutyl)imidazo[1,5-a]pyridine, melting at 195°–197°.

EXAMPLE 22

2-Aminomethyl-5-(4-methoxycarbonylbutyl)pyridine (0.20 g) is heated at 90° in 0.6 ml of formic acid for 18 hours. The mixture is cooled to 0°, made basic with saturated ammonium hydroxide solution and extracted with methylene chloride (4×15 ml). Drying, filtration and evaporation of the extracts yields 2-(N-formylaminomethyl)-5-(4-methoxycarbonylbutyl)pyridine as an oil (IR 1720, 1675 cm$^{-1}$) which is redissolved in 1 ml of toluene and heated at 90° for 18 hours with phosphorus oxychloride (0.166 g). Evaporation of excess phosphorus oxychloride with toluene, basification at 0° with saturated ammonium hydroxide solution, extraction with methylene chloride (4×15 ml) and drying over sodium sulfate yields an oil which is chromatographed (silica gel, ethyl acetate) to yield 6-(4-methoxycarbonylbutyl)-imidazo[1,5-a]pyridine; Rf=0.26; NMR (CDCl$_3$) 3.58 (s, 3H), 6.45 (d, 1H), 7.25 (d, 1H), 7.38 (s, 1H), 7.62 (s, 1H), 7.94 (s, 1H); IR (CH$_2$Cl$_2$) 1730 cm$^{-1}$.

The starting material is prepared as follows:

2-Cyano-5-(4-methoxycarbonylbutyl)pyridine (1.48 g, see Example 20) is dissolved in 56 ml of methanol containing 1.5 ml of concentrated hydrochloric acid and hydrogenated at atmospheric pressure with 0.75 g of 10% palladium on charcoal for 18 hours. Filtration, evaporation, chromatography on 20 g of silica gel with 1:1 methanol-ethyl acetate, and crystallization from ether-methylene chloride yields 2-aminomethyl-5-(4-methoxycarbonylbutyl)pyridine as its carbonate melting at 79°–80°; NMR (CDCl$_3$) 3.67 (s, 3H), 4.24 (s, 2H); IR (CH$_2$Cl$_2$) 1725 cm$^{-1}$.

EXAMPLE 23

A solution of 6-(4-methoxycarbonylbutyl)-imidazo[1,5-a]pyridine in 0.3 ml of ethanol and 0.8 ml of 1N sodium hydroxide, is refluxed gently for 2 hours, cooled, diluted with 2 ml of water and extracted with ethyl acetate (5 ml). The aqueous phase is brought to pH=6 and is extracted with chloroform. The extracts are dried and evaporated to yield 6-(4-carboxybutyl)-imidazo[1,5-a]pyridine, melting at 168°-171°.

EXAMPLE 24

2-(N-formylaminomethyl)-4-(3-methoxycarbonylpropyl)pyridine (33 mg) is dissolved in 1 ml of toluene and heated at 90° with phosphorus oxychloride (44 mg) for 18 hours under nitrogen. The solvent is evaporated and the residue is suspended in methylene chloride, cooled to 0° and made basic with saturated ammonium hydroxide solution. The aqueous phase is extracted with methylene chloride (4×15 ml) which is dried over sodium sulfate and evaporated to yield 7-(3-methoxycarbonylpropyl)imidazo[1,5-a]pyridine as an oil, after purification by preparative thin layer chromatography (silica gel, 3:1 ethyl acetate-methanol); NMR (CDCl$_3$) 3.70 (s, 3H); 6.45 (q, 1H), 7.2 (s, 1H), 7.32 (s, 1H), 7.90 (d, 1H); 8.08 (s, 1H); IR (CH$_2$Cl$_2$) 1730 cm$^{-1}$.

The starting material is prepared as follows:

Potassium cyanide (11.18 g) and dibenzo-18-crown-6 (1.0 g) are added to a solution of 4-(3-chloropropyl)pyridine (6.68 g) prepared from 4-(3-hydroxypropyl)pyridine, in 300 ml of dry acetonitrile under nitrogen. The mixture is refluxed for 24 hours, the solvent evaporated and the residue partitioned between methylene chloride and water. The aqueous phase is further extracted with methylene chloride (3×100 ml) and the combined extracts are dried over sodium sulfate, decolorized with charcoal and evaporated to yield 4-(3-cyanopropyl)pyridine as a colorless oil.

Hydrogen chloride is bubbled slowly into an ice-cooled methanolic solution of 4-(3-cyanopropyl)pyridine (5.5 g) for 2 hours and 100 ml of water is added carefully. The solution is stirred for 15 minutes and the solvent is evaporated. The residue is made basic with saturated sodium bicarbonate solution and extracted with methylene chloride (3×100 ml) which is dried over sodium sulfate. Evaporation of the solvent and filtration through 50 g of silica gel in ether yields 4-(3-methoxycarbonylpropyl)pyridine as an oil; NMR (CDCl$_3$) 3.68 (s, 3H), 7.05-7.25 (m, 2H), 8.45-8.56 (m, 2H); IR, 1725 cm$^{-1}$.

Peracetic acid (40%, 2.9 ml) is added to 4-(3-methoxycarbonylpropyl)pyridine (3.20 g) at room temperature. The mixture is heated at 80° for 1 hour and the acetic acid is evaporated after a test for peroxide is negative. The residue is taken up in methylene chloride (50 ml), filtered, and the solvent evaporated. The resulting 4-(3-methoxycarbonylpropyl)pyridine-N-oxide is treated with dimethyl sulfate (2.8 g) in 12 ml of toluene at 80° for 1 hour. The solvent is evaporated to yield 5.45 g of the 4-(3-methoxycarbonylpropyl)-1-methoxypyridinium methyl sulfate salt which is added at 0° to a solution of 89.75 g potassium cyanide in 20 ml of water. The reaction is stirred at 0° for 1 hour and 25° for 3 hours and then extracted with methylene chloride (1×30 ml). The aqueous phase is reextracted, after standing for 24 hours, with methylene chloride (1×30 ml), and the combined extracts are dried over sodium sulfate and evaporated to yield a red oil. Chromatography on 70 g of silica gel with ether as the eluent yields 2-cyano-4-(3-methoxycarbonylpropyl)pyridine as an oil; NMR (CDCl$_3$) 3.67 (s, 3H), 7.42 (d, 1H), 7.60 (s, 1H), 8.60 (d, 1H); IR (CH$_2$Cl$_2$) 1725 cm$^{-1}$.

2-Cyano-4-(3-methoxycarbonylpropyl)pyridine (0.83 g) is hydrogenated at 3 atmospheres for 3 hours in 9 ml of methanol with 0.4 g of 10% palladium on charcoal. Filtration, evaporation, and preparative thin layer chromatography on silica gel with 1:1 methanol-ethyl acetate yields 2-aminomethyl-4-(3-methoxycarbonylpropyl)pyridine; Rf, 0.37 (EtOAc-MeOH 1:1, 1% NH$_4$OH); NMR (CDCl$_3$) 3.67 (s, 3H), 4.15 (s, 2H).

2-Aminomethyl-4-(3-methoxycarbonylpropyl)pyridine (0.11 g) is heated at 90° in 0.5 ml of 97% formic acid for 18 hours. The reaction is cooled to room temperature, made basic with ammonium hydroxide solution and extracted with methylene chloride (4×20 ml). The organic extracts are dried over sodium sulfate and evaporated to yield 2-(N-formylaminomethyl)-4-(3-methoxycarbonylpropyl)pyridine; IR (CH$_2$Cl$_2$) 1735, 1685 cm$^{-1}$.

EXAMPLE 25

7-(3-methoxycarbonylpropyl)-imidazo[1,5-a]pyridine (Example 24, 8.0 mg) is dissolved in 0.3 ml of methanol and 0.1 ml of 1N NaOH is added. The mixture is stirred at 25° for 5 hours, evaporated, and the residue is redissolved in 5 ml of water. The aqueous solution is washed with 2 ml of ethyl acetate, brought to pH=6 with 2N sulfuric acid and extracted with methylene chloride (3×5 ml). The organic extracts are dried over sodium sulfate/magnesium sulfate and evaporated to yield 7-(3-carboxypropyl)-imidazo[1,5-a]pyridine, IR (CHCl$_3$) 1720 cm$^{-1}$.

EXAMPLE 26

A solution of 7-[4,4-(bis-methoxycarbonyl)butyl]-imidazo[1,5-a]pyridine (65 mg) in 0.8 ml of 1N sodium hydroxide and 0.5 ml of ethanol is heated at reflux for 2 hours. The solvent is evaporated and 0.8 ml of 1N hydrochloric acid is added. After the water is evaporated, the residue is redissolved in 3 ml of xylene and heated at 137° for 4 hours. The xylene is evaporated and replaced with 2 ml of 1N sodium hydroxide. Extraction of the aqueous phase with ethyl acetate (5 ml), acidification to pH=6, reextraction with chloroform (3×15 ml) and evaporation yields 7-(4-carboxybutyl)imidazo[1,5-a]pyridine, melting at 158°-161°.

The starting material is prepared as follows:

According to procedures previously described (e.g., Examples 20, 24), 4-(3-chloropropyl)pyridine is converted to 4-(3-chloropropyl)-2-cyanopyridine; NMR (CDCl$_3$) 3.56 (t, 2H), 7.40 (d, 1H), 7.57 (s, 1H), 8.60 (d, 1H).

A solution of borane-dimethylsulfide (0.83 ml, 7.7 mmol) in 7 ml of tetrahydrofuran is added slowly to a refluxing solution of 4-(3-chloropropyl)-2-cyanopyridine (1.24 g, 6.9 mmol) in 7 ml of tetrahydrofuran while dimethylsulfide simultaneously distills off. The mixture is refluxed for 15 minutes after the addition is complete, cooled to 30° and 6 ml of 6N hydrochloric acid is added. After hydrogen evolution ceases, the mixture is refluxed for 30 minutes, cooled to 0° and saturated with solid sodium carbonate before extracting with methylene chloride (4×50 ml). The organic extracts are dried over sodium sulfate and evaporated to yield an oil which is filtered through 10 g of silica gel (1:1 EtOAc-MeOH) to yield 2-aminomethyl-4-(3-chloropropyl)pyridine as a yellow oil; NMR (CDCl$_3$) 3.55 (t, 2H), 4.20 (s, 2H).

A solution of 2-aminomethyl-4-(3-chloropropyl)pyridine (0.47 g) in 1 ml of formic acid is heated at 90° for 18 hours, cooled to 0° and made basic by the addition of saturated ammonium hydroxide solution. Extraction with methylene chloride (4×10 ml), drying over sodium sulfate and evaporation yields 2-(N-formylaminomethyl)-4-(3-chloropropyl)pyridine (IR 1674 cm$^{-1}$) which is heated at 90° in phosphorus oxychloride (0.75 g) for 15 hours. Excess phosphorus oxychloride is evaporated with toluene and the residue is suspended in methylene chloride (15 ml), cooled to 0° and made basic with saturated ammonium hydroxide. Extraction with methylene chloride (4×15 ml), drying over sodium sulfate and preparative thin layer chromatography (silica gel, EtOAc) of the residue yields 7-(3-chloropropyl)-imidazo[1,5-a]pyridine (Rf=0.24, EtOAc) as a gum; NMR (CDCl$_3$) 3.58 (t, 2H), 6.42 (q. 1H), 7.21 (s, 1H), 7.32 (s, 1H), 7.88 (d, 1H, 8.07 (s, 1H).

A solution of 7-(3-chloropropyl)-imidazo[1,5-a]pyridine (50 mg), dimethyl malonate (0.14 g), and potassium carbonate (144 mg) in 2 ml of dimethylformamide is heated between 80° and 90° under nitrogen for 9 hours. The solvent is evaporated and the residue taken up in 10 ml of water and extracted with ethyl acetate (2×10 ml). The organic extracts are washed with 2N hydrochloric aid (2×10 ml). Basification of the aqueous extracts with solid sodium bicarbonate, extraction with methylene chloride (3×10 ml), drying over sodium sulfate and evaporation yields 7-[4,4-(bis-methoxycarbonyl)butyl-]imidazo[1,5-a]pyridine; NMR (CDCl$_3$) 3.40 (s, 6H), 6.06 (d, 1H); IR (CH$_2$Cl$_2$) 1725 cm$^{-1}$.

EXAMPLE 27

5-(4-Chlorobutyl)-imidazo[1,5-a]pyridine is prepared by the procedure described for the preparation of 5-(5-chloropentyl)imidazo[1,5-a]pyridine of Example 4 using 1-bromo-3-chloropropane as reagent instead of 1-bromo-4-chlorobutane therein.

EXAMPLE 28

The condensation of 6-benzyloxy-5-methylimidazo[1,5-a]pyridine with 5-bromo-1,1,1-triethoxypentane essentially by the procedure described in Example 1 yields 6-benzyloxy-5-(5-ethoxycarbonylpentyl)-imidazo[1,5-a]pyridine; NMR (CDCl$_3$) 1.4 (3H), 4.17 (2H), 4.97 (2H).

Hydrolysis with 1N aqueous sodium hydroxide, ethanol (1:1) yields 6-benzyloxy-5-(5-carboxypentyl-)imidazo[1,5-a]pyridine, m.p. 139°-141°.

The starting 6-benzyloxy-5-methylimidazo[1,5-a]pyridine is prepared as follows:

A solution of 3-benzyloxy-6-hydroxymethyl-2-methylpyridine (8.54 g) in 53 ml of thionyl chloride is refluxed for two hours and the thionyl chloride is removed by distillation. The residue is poured onto 50 g of ice, made basic with saturated sodium bicarbonate solution and extracted with ethyl acetate (3×50 ml). The organic extracts are dried over sodium sulfate and evaporated to give a yellow oil identified as 3-benzyloxy-6-chloromethyl-2-methylpyridine; NMR: (CDCl$_3$) 2.47 (3H), 4.54 (2H), 4.97 (2H).

A solution of 3-benzyloxy-6-chloromethyl-2-methylpyridine (8.02 g) and sodium azide (5.98 g) in 400 ml of ethanol is heated at 80° for 4 hours. The reaction mixture is cooled, filtered and evaporated to yield a residue which is partitioned between ice-cold 0.5N NaOH (150 ml) and ether (150 ml). The organic phase is dried over sodium sulfate and evaporated to yield 6-azidomethyl-3-benzyloxy-2-methylpyridine, NMR: (CDCl$_3$) 2.47 (3H), 4.27 (2H), 4.95 (2H). Lithium aluminum hydride (1.27 g) is added to a solution of 6-azidomethyl-3-benzyloxy-2-methylpyridine (7.18 g) in 120 ml of dry ether at room temperature. After stirring for 45 minutes, 1.3 ml of water, 1.3 ml of 15% sodium hydroxide and 3.8 ml of water are added sequentially. The salts are filtered off and the filtrate is evaporated to yield 6-aminomethyl-3-benzyloxy-2-methylpyridine; NMR: (CDCl$_3$) 1.67 (2H), 2.47 (3H), 3.8 (2H), 4.95 (2H).

A solution of 6-aminomethyl-3-benzyloxy-2-methylpyridine (6.31 g) in 8.7 ml of formic acid is heated at 90° for 15 hours. The reaction mixture is cooled, made basic with ice-cold ammonium hydroxide solution and extracted with chloroform. (3×25 ml). The chloroform extract is dried over sodium sulfate and evaporated. Recrystallization from ether yields 3-benzyloxy-6-formylaminomethyl-2-methylpyridine, m.p. 67°-68°.

A solution of 3-benzyloxy-6-formylaminomethyl-2-methylpyridine (5.14 g) and phosphorus oxychloride (4.0 ml) in 18 ml of toluene is heated at 90° for 15 hours. The solvent is evaporated and the residue taken up in chloroform (50 ml), cooled to 0° and made basic with ice-cold ammonium hydroxide solution. The aqueous phase is further extracted with chloroform (3×20 ml) and the organic phase is dried over sodium sulfate. Evaporation yields an oil (3.84 g) which is passed through 38 g of silica gel with ethyl acetate. Recrystallization of the resulting solid from ether yields 6-benzyloxy-5-methylimidazo[1,5-a]pyridine, m.p. 52°-54°.

EXAMPLE 29

(a) A mixture of 5-(4-cyanobutyl)-imidazo[1,5-a]pyridine (4.0 g), sodium azide (1.88 g), ammonium chloride (1.57 g) and lithium chloride (10 mole %) in 14 ml of dry dimethylformamide is heated at 125° for 17 hours. The reaction mixture is cooled, filtered and evaporated to a residual oil which is redissolved in 50 ml of water and extracted with ethyl acetate (50 ml). The aqueous phase is adjusted to pH=2 and extracted with ethyl acetate and then adjusted to pH=5. The resulting solid is collected by filtration and converted to its hydrochloride salt which is recrystallized from acetone/methanol to yield 5-[4-(5-tetrazolyl)butyl]-imidazo[1,5-a]pyridine monohydrochloride, m.p. 159°-161°.

The starting materials are prepared as follows:

A solution of 5-(4-chlorobutyl)imidazo[1,5-a]pyridine (5.73 g), potassium cyanide (7.18 g) and 1.0 g of dibenzo-18-crown-6 in 190 ml of acetonitrile is heated at reflux for 18 hours, cooled and evaporated to a residual oil which is partitioned between water and methylene chloride. The organic phase is dried over sodium sulfate and evaporated. The resulting solid is dissolved in ethyl acetate and filtered through 60.0 g of silica gel to yield 5-(4-cyanobutyl)-imidazo[1,5-a]pyridine m.p. 72°-75°.

EXAMPLE 30

A solution of 5-(5-cyanopentyl-imidazo[1,5-a]pyridine (5.26 g) in 16 ml of dry dimethylformamide is heated at 120° for 15 hours with sodium azide (2.15 g), lithium chloride (0.2 g) and ammonium chloride (1.80 g). After cooling and filtering, the solvent is evaporated and the residue is dissolved in 50 ml of water, extracted with 25 ml of ethyl acetate and brought to pH=5 with concentrated sulfuric acid. The precipitated solid is filtered, washed with water and dried to yield 5-[5-(5-tetrazolyl)pentyl]imidazo[1,5-a]pyridine, m.p. 149°-150°. The mono-hydrochloride salt has m.p. 188°-190°.

The starting material (see Example 4) is also prepared as follows:

Thionyl chloride (11.42 g) is added slowly at room temperature to a suspension of 5-(5-carboxypentyl-)imidazo[1,5-a]pyridine (21.0 g) and sulfamide (10.5 g)

in 90 ml of sulfolane. The mixture is heated at 120° until gas evolution ceases and solid p-toluenesulfonic acid monohydrate (1.71 g) is added carefully. After heating an additional 3 hours at 120°, the reaction mixture is cooled, poured onto 200 g of ice and acidified with 130 ml of 1N hydrochloric acid. The aqueous phase is sequentially extracted with ethyl acetate (3×100 ml), made basic with solid sodium bicarbonate and reextracted with ethyl acetate (3×125 ml). The organic extracts are washed with 0.5N sodium hydroxide (5×50 ml), dried over sodium sulfate and evaporated to yield an oil which is chromatographed on 60 g of silica gel with ethyl acetate to yield 5-(5-cyanopentyl)-imidazo[1,5-a]pyridine as an oil.

EXAMPLE 31

A solution of hydroxylamine (from 2.06 g of hydroxylamine hydrochloride and 2.02 g of sodium hydroxide) and 5-(5-methoxycarbonylpentyl)imidazo[1,5-a]pyridine (6.08 g) in 25 ml of methanol is allowed to stand at room temperature for 20 hours. The methanol is evaporated and the residue is taken up in 5 ml of water and adjusted to pH=7. The resulting oil crystallizes and the solid is collected, yielding 5-[5-(hydroxycarbamoyl)-pentyl]-imidazo[1,5-a]-pyridine, m.p. 138°–140°.

EXAMPLE 32

Ethanolamine (6.1 g) and 5-(5-carboxypentyl)-imidazo[1,5-a]pyridine (2.32 g) are heated at 170° for 3 hours. Excess ethanolamine is removed by distillation under reduced pressure to yield 5-[5-(4,5-dihydrooxazol-2-yl)pentyl)]imidazo[1,5-a]pyridine.

EXAMPLE 33

Preparation according to methods analogous to those described in the previous examples of compounds of formula I wherein B represents 5-tetrazolyl or hydroxycarbamoyl. "Position" indicates the point of attachment of the —CH$_2$—A—B chain.

| No. | Position | A | R$_1$ | R$_2$ |
|---|---|---|---|---|
| 1 | 5 | (CH$_2$)$_4$ | 6-benzyloxy | H |
| 2 | 5 | (CH$_2$)$_2$CH=CH | H | H |
| 3 | 5 | (CH$_2$)$_4$CH=CH | H | H |
| 4 | 8 | (CH$_2$)$_3$ | H | H |
| 5 | 6 | (CH$_2$)$_3$ | H | H |
| 6 | 7 | (CH$_2$)$_2$ | H | H |
| 7 | 7 | (CH$_2$)$_3$ | H | H |
| 8 | 5 | (CH$_2$)$_5$ | H | 3-CH$_3$ |
| 9 | 5 | (CH$_2$)$_4$ | 6-methoxy | H |

Starting material for compound 8: 3,5-dimethylimidazo[1,5-a]pyridine, J. Het. Chem. 3, 33 (1966).

EXAMPLE 24

Preparation of 10,000 tablets each containing 10 mg of active ingredient:

| Formula: | |
|---|---|
| 5-[4-(5-tetrazolyl)butyl]-imidazo[1,5-a]pyridine | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension is added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 35

Preparation of 10,000 capsules each containing 25 mg of the active ingredient:

| Formula: | |
|---|---|
| 5-[5-(hydroxycarbamoyl)pentyl]-imidazo[1,5-a]pyridine | 250.0 g |
| Lactose | 1650.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg., using a capsule filling machine.

Similarly prepared are tablets and capsules comprising about 10–100 mg of other compounds of the invention, e.g. any other compound given in the examples herein.

What is claimed is:

1. A compound of the formula

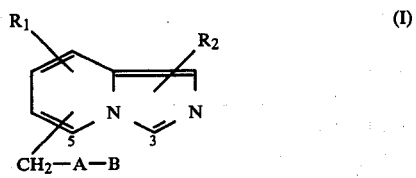

or a 5,6,7,8-tetrahydro derivative thereof, wherein R$_1$ is hydrogen, halogen, lower alkyl, lower alkoxy, hydroxy, or aryl-lower alkoxy in which aryl is phenyl or phenyl mono- or disubstituted by lower alkyl, halogen or lower alkoxy; R$_2$ is hydrogen, halogen or lower alkyl; A is straight chain or branched alkylene of 1 to 12 carbon atoms, alkynylene or alkenylene of 2 to 12 carbon atoms each; B represents 5-tetrazolyl, hydroxycarbamoyl, 4,5-dihydro-2-oxazolyl or 4,5-dihydro-2-oxazolyl substituted by lower alkyl; or a pharmaceutically acceptable salt thereof.

2. A compound of claim 1 wherein the group CH$_2$—A—B is at the 5-position.

3. A compound of claim 1 wherein A is straight or branched alkylene of 1 to 12 carbon atoms.

4. A compound of claim 1 of the formula

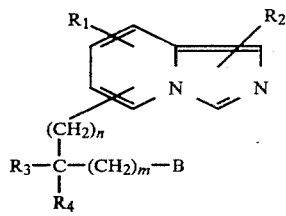

or a 5,6,7,8-tetrahydro derivative thereof, wherein $R_1$, $R_2$, $R_3$ and $R_4$ are hydrogen or lower alkyl of 1 to 4 carbon atoms; n is 1 to 7; m is 0 or 1; B is 5-tetrazolyl, hydroxycarbamoyl, 4,5-dihydro-2-oxazolyl or 4,5-dihydro-2-oxazolyl substituted by lower alkyl; or a pharmaceutically acceptable salt thereof.

5. A compound of claim 4 wherein the group

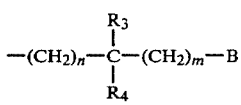

is attached at the 5-position.

6. A compound of claim 4, or a 5,6,7,8-tetrahydro derivative thereof, wherein $R_1$, $R_2$, $R_3$, $R_4$ are hydrogen, methyl or ethyl; $(CH_2)_n$ is propylene, butylene, pentylene or hexylene, m is 0 or 1; B represents 5-tetrazolyl, hydroxycarbamoyl, 4,5-dihydro-2-oxazolyl; or a pharmaceutically acceptable salt thereof.

7. A compound of claim 1 of the formula

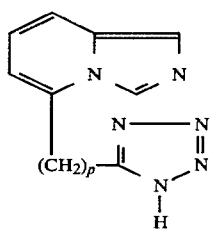

or a 5,6,7,8-tetrahydro derivative thereof, wherein p is 3 to 8; B represents 5-tetrazolyl or hydroxycarbamoyl; or a pharmaceutically acceptable salt thereof.

8. A compound of claim 7, the compound being 5-[4-(5-tetrazolyl)-butyl]-imidazo[1,5-a]pyridine or a pharmaceutically acceptable acid or base addition salt thereof.

9. A compound of claim 7, the compound being 5-[5-(5-tetrazolyl)-pentyl]-imidazo[1,5-a]pyridine or a pharmaceutically acceptable acid of base addition salt thereof.

10. A compound of claim 1, the compound being 5-[5-(hydroxycarbamoyl)pentyl]imidazo[1,5-a]pyridine or a pharmaceutically acceptable acid or base addition salt thereof.

11. A pharmaceutical composition suitable for oral or parenteral administration to mammals for the treatment or prevention of diseases responsive to inhibition of thromboxane synthetase comprising an effective amount of a compound of claim 1 in combination with one or more pharmaceutically acceptable carriers.

12. A method of selectively inhibiting the release of thromboxane in mammals comprising the administration to a mammal of an effective amount of a compound of claim 1.

13. A method of treating diseases responsive to thromboxane synthetase inhibition in mammals comprising the administration to a mammal in need thereof of a therapeutically effective amount of a compound of claim 1.

14. A method of treating diseases responsive to thromboxane synthetase inhibition in mammals comprising the administration of a therapeutically effective amount of a pharmaceutical composition of claim 11.

15. A compound of the formula

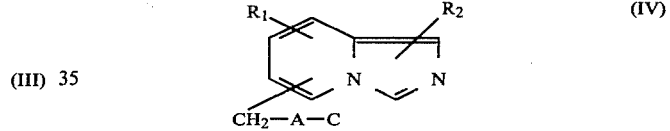

wherein $R_1$ is lower alkoxy or aryl-lower alkoxy; $R_2$ is hydrogen or lower alkyl; A is straight chain or branched alkylene of 3 to 8 carbon atoms, alkynylene or alkenylene of 4 to 8 carbon atoms each; C is carboxy, lower alkoxycarbonyl, carbamoyl or cyano; or a pharmaceutically acceptable salt thereof.

16. A compound of claim 15 wherein C is carboxy; or a pharmaceutically acceptable salt thereof.

17. A compound of claim 15 being 6-benzyloxy-5-(carboxypentyl)imidazo[1,5-a]pyridine or a pharmaceutically acceptable salt thereof.

* * * * *